US011191296B2

(12) United States Patent
Abehasera

(10) Patent No.: US 11,191,296 B2
(45) Date of Patent: Dec. 7, 2021

(54) SMART GRINDER

(71) Applicant: TRI Innovations, LLC, Hallandale Beach, FL (US)

(72) Inventor: Benyamin Abehasera, Hallandale Beach, FL (US)

(73) Assignee: TRI Innovations, LLC, Hallandale Beach, FL (US)

( * ) Notice: Subject to any disclaimer, the term of this patent is extended or adjusted under 35 U.S.C. 154(b) by 0 days.

(21) Appl. No.: 17/333,596

(22) Filed: May 28, 2021

(65) Prior Publication Data

US 2021/0282447 A1 Sep. 16, 2021

Related U.S. Application Data

(63) Continuation-in-part of application No. 16/285,609, filed on Feb. 26, 2019, now Pat. No. 11,051,657.

(51) Int. Cl.
| | |
|---|---|
| *A47J 42/00* | (2006.01) |
| *A24B 7/04* | (2006.01) |
| *B02C 23/24* | (2006.01) |
| *A24B 7/14* | (2006.01) |
| *B08B 1/00* | (2006.01) |

(Continued)

(52) U.S. Cl.
CPC ............... *A24B 7/04* (2013.01); *A24B 7/14* (2013.01); *A46B 13/02* (2013.01); *A47J 42/00* (2013.01); *A47J 42/22* (2013.01); *A47J 42/28* (2013.01); *A61L 2/10* (2013.01); *A61L 2/24* (2013.01); *A61L 2/26* (2013.01); *B02C 23/24* (2013.01); *B08B 1/002* (2013.01); *B08B 1/04* (2013.01); *B08B 9/00* (2013.01); *A46B 2200/3006* (2013.01); *A61L 2202/11* (2013.01); *A61L 2202/14* (2013.01)

(58) Field of Classification Search
CPC .. A47J 42/00; A47J 42/22; A47J 42/28; A47J 42/36; A47J 42/40; A47J 42/46; A47J 42/16; A47J 42/56; A47J 42/06; A24B 7/14
See application file for complete search history.

(56) References Cited

U.S. PATENT DOCUMENTS 2,029,192 A * 1/1936 Ray .................... A24F 19/0042
131/240.1
4,469,283 A * 9/1984 Noguchi ................. A47J 42/40
241/282.1

(Continued)

*Primary Examiner* — Faye Francis
(74) *Attorney, Agent, or Firm* — Geoffrey Lottenberg; Berger Singerman LLP

(57) ABSTRACT

A electronic grinder includes a main body and a grinding and dispensing chamber. The top of the main body open but covered by a cap. The main chamber includes a motor connected to a magnetically attached removable blade and propeller. The blade and propeller extend into the chamber when the grinder is assembled. When the cap is closed, the blade and propeller grinds material placed in the chamber and pull air down toward the blade and propeller. When the cap is opened, the blade and propeller function as a fan to generate airflow toward the top of the chamber to dispense ground material out of the chamber. The grinder can also include a microcontroller, a communications device, an infrared volume sensor, a scale, an audible buzzer, a vibration buzzer, and one or more sanitizing LED lights.

20 Claims, 4 Drawing Sheets

(51) Int. Cl.

| | | |
|---|---|---|
| *B08B 1/04* | (2006.01) | |
| *A46B 13/02* | (2006.01) | |
| *A61L 2/10* | (2006.01) | |
| *A61L 2/24* | (2006.01) | |
| *A61L 2/26* | (2006.01) | |
| *B08B 9/00* | (2006.01) | |
| *A47J 42/22* | (2006.01) | |
| *A47J 42/28* | (2006.01) | |

(56) References Cited

U.S. PATENT DOCUMENTS

| | | | | | |
|---|---|---|---|---|---|
| 4,875,630 | A * | 10/1989 | Carlson | | A01D 51/00 241/56 |
| 5,245,726 | A * | 9/1993 | Rote | | A01G 20/47 15/339 |
| 5,687,746 | A * | 11/1997 | Rose | | A61M 15/06 131/273 |
| D529,769 | S * | 10/2006 | Tardif | | D7/679 |
| D576,452 | S * | 9/2008 | Kavanaugh | | D7/679 |
| D576,453 | S * | 9/2008 | Kavanaugh | | D7/679 |
| 7,422,170 | B2 * | 9/2008 | Bao | | B02C 18/24 241/168 |
| 9,427,020 | B2 * | 8/2016 | Ruzycky | | B02C 18/144 |
| 9,737,092 | B2 * | 8/2017 | Grumbacher | | A24C 5/40 |
| 10,086,381 | B2 * | 10/2018 | Cottam | | B02C 18/18 |
| 10,478,825 | B2 * | 11/2019 | Mroue | | B02C 18/10 |
| D871,668 | S * | 12/2019 | Lee | | D27/194 |
| D885,653 | S * | 5/2020 | Ding | | D27/162 |
| 11,051,657 | B2 * | 7/2021 | Abehasera | | A47J 42/28 |
| 2005/0016554 | A1 * | 1/2005 | Carbonell | | A47J 42/28 131/328 |
| 2008/0237380 | A1 * | 10/2008 | Kalogroulis | | A47J 42/46 241/169.1 |
| 2013/0025608 | A1 * | 1/2013 | Fakhouri | | A24F 9/00 131/311 |
| 2014/0182604 | A1 * | 7/2014 | Hutton | | A24C 5/42 131/70 |
| 2014/0182608 | A1 * | 7/2014 | Egoyants | | A24F 40/485 131/328 |
| 2014/0209105 | A1 * | 7/2014 | Sears | | A24F 40/46 131/328 |
| 2014/0353412 | A1 * | 12/2014 | Grumbacher | | A24C 5/40 241/70 |
| 2015/0257599 | A1 * | 9/2015 | Ng | | A23K 20/163 426/518 |
| 2016/0106262 | A1 * | 4/2016 | Mroue | | A47J 42/30 241/79 |
| 2017/0252752 | A1 * | 9/2017 | Cottam | | B02C 23/26 |
| 2017/0259273 | A1 * | 9/2017 | Cottam | | B02C 7/04 |
| 2017/0319009 | A1 * | 11/2017 | Seckel | | B02C 18/2216 |
| 2018/0020735 | A1 * | 1/2018 | Bilat | | H05B 3/44 131/328 |
| 2018/0103805 | A1 * | 4/2018 | Huang | | B02C 19/08 |
| 2018/0213838 | A1 * | 8/2018 | Richmond | | A24C 5/44 |
| 2018/0271328 | A1 * | 9/2018 | Petrossian | | A47J 42/24 |
| 2018/0296037 | A1 * | 10/2018 | Tseng | | B65G 33/34 |
| 2019/0159631 | A1 * | 5/2019 | Wafa | | A47G 19/2205 |
| 2020/0113369 | A1 * | 4/2020 | Bardot | | A47J 31/20 |
| 2020/0221904 | A1 * | 7/2020 | Girardi | | A47J 42/36 |
| 2020/0269254 | A1 * | 8/2020 | Abehasera | | A47J 42/36 |
| 2020/0345061 | A1 * | 11/2020 | Veelo | | B02C 25/00 |
| 2021/0015146 | A1 * | 1/2021 | Chaben | | A24B 7/14 |

* cited by examiner

SMART GRINDER

CROSS REFERENCE TO RELATED APPLICATIONS

This application is a continuation-in-part of U.S. patent application Ser. No. 16,285,609 filed on Feb. 26, 2019.

FIELD OF THE INVENTION

The present invention relates to the technical field of grinders, more particularly to an electronic grinder adapted for grinding and pulverizing herbs and other materials.

BACKGROUND OF THE INVENTION

In daily life, people gradually begin to have personalized demands for smoking a small amount of tobacco or refined tobacco, hemp plants, hemp flowers, spices and herbs. Most of these products have to be pulverized or ground in order to effectively smoke. When grinding or pulverizing a variety of herbs, people have different requirements on the size and shape of the blades due to the difference in dryness, hardness and viscosity of different herbs. However, existing rotary shaft grinders usually have the blade fixedly connected to the shaft, therefore the blade cannot be easily replaced, thereby limiting the user to a single mode of pulverization. Additionally, portability has become a key market force in many categories, with users desiring small and more feature-packed electronic devices to serve their daily needs. Accordingly there is a need to improve upon the existing art and provide a more versatile and portable electronic grinder.

DETAILED DESCRIPTION

In the following description, for the purposes of explanation, numerous specific details are set forth in order to provide a thorough understanding of the present invention. It will be apparent, however, to one skilled in the art that the present invention may be practiced without some of these specific details. Throughout this description, the embodiments and examples shown should be considered as exemplars, rather than as limitations on the invention. That is, the following description provides examples, and the accompanying drawings show various examples for the purposes of illustration. However, these examples should not be construed in a limiting sense as they are merely intended to provide examples of the invention rather than to provide an exhaustive list of all possible implementations thereof.

Specific embodiments of the invention will now be further described by the following, non-limiting examples which will serve to illustrate various features. The examples are intended merely to facilitate an understanding of ways in which the invention may be practiced and to further enable those of skill in the art to practice the invention. Accordingly, the examples should not be construed as limiting the scope of the invention. In addition, reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner in one or more embodiments.

Figure 1A:
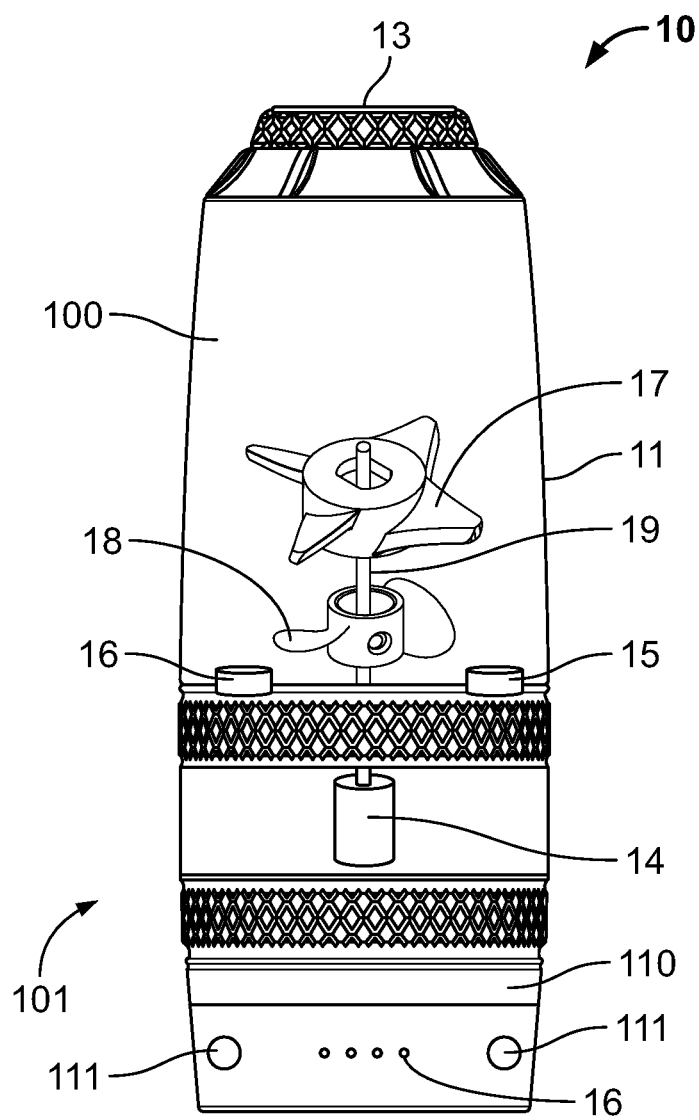
FIG. 1A is a schematic of the grinder.

Referring to FIG. 1A, the multi-function electronic grinder 10 of the present invention comprises a main housing 11 comprising a dispensing chamber 100 a base 101. In some embodiments, the dispensing chamber 100 is removable from the base 101 to permit access to device components for cleaning and changing components as further described herein. In some embodiments, the distal end of the main housing 11 includes a removable cap 13 which covers an open top from which material is dispensed. In some embodiments, the cap 13 engages the housing 11 by snap fit, threads, magnetic connection, or the like. In some embodiments, the cap 13 is magnetically but removably latched distal end of the main housing 11 so that it remains closed until sufficient manual force is applied to break the magnetic connection. The cap 13 is thus openable to provide a point of exit to dispense ground material from the chamber and out of the grinder 10.

The main housing 11 comprises and contains the various electronic components of the grinder including a motor 14, one or more LED lights 15, a battery capacity indicator 16, and one or more input buttons 111. A power source 101, such as a battery (rechargeable or otherwise) or external power supply, provides power to the motor 14 and other components of the grinder. The motor 14 drives a blade 17 and/or a propellor 18 by way of a drive shaft 19 extending from the motor 14. In some embodiments, the blade 17 and/or propellor 18 is removably attached to the drive shaft 19 such that they can be removed for cleaning or replacement. In some embodiments, the blade 17 and/or propellor 18 is magnetically but removably attached to the drive shaft 19 for easy manual replacement. In some embodiments, the LED lights 15 are configured to emit light of a wavelength in the range of 100-280 nm and, more particularly, in the range of 200-280 nm, which is considered the UVC range effective for killing microorganisms such as bacteria, viruses, and the like.

Figure 1B:
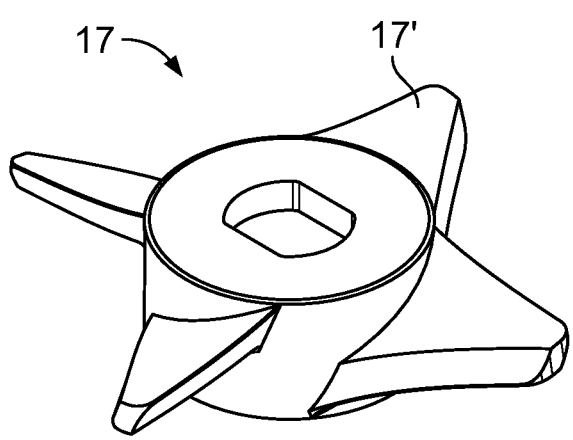
FIG. 1B is a perspective view of a curved blade of the grinder.
Figure 1C:
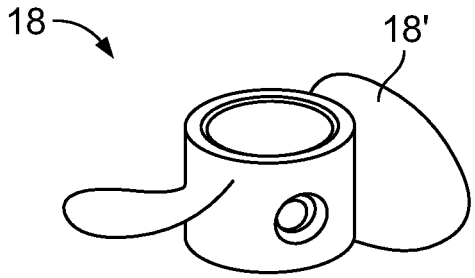
FIG. 1C is a perspective view of a fan propeller of the grinder.

The blade 17 and propellor 18 are seated inside the chamber 100 to effectively grind and pulverize material placed in the chamber 100. With reference to FIGS. 1B and 1C, in some embodiments, the blade 17 has a relatively flat, horizontal configuration with the blade elements 17' having a curved profile with beveled edges. In this configuration, the blade 17 functions to cut and grind material while also introducing air-turbulence to dry the material and to assist with the dispensing of the material out of the chamber 100 with the cap 13 open. Also provided in propellor 18 which may be disposed above or below the blade 17 along the drive shaft 19. In some embodiments, the angle of the blade elements 17' of the blade 17' are shallower than that of the blade elements 18' of the propellor 18. The propellor functions as a fan to introduce air flow to either pull the material down into the blade 17 or dispense and expel material from the chamber 100, depending on the direction of rotation of the motor 14. In some embodiments, the air flow generating function of the blade 17 is supplemental to the air flow generated by the propellor 18.

It is apparent that the blade/propellor combination functions to grind and dispense material out of the chamber 100. In some embodiments, the blade 17 and propeller 18 (either separately or together) can be configured to function as a grinder when rotating in one direction whereby the blade 17 and/or the propeller 18 pull air down toward the blade 17 which draws the material into the blade 17 for efficient grinding. Conversely, the blade 17 and propeller 18 can be configured to function as a fan when rotating in another direction, wherein the air flow is generate away from the blade 17 and propeller 18 toward the open top of the grinder 18. Accordingly, the direction of the blade 17 and propeller 18 can be reversed in order to force air out of the chamber and out toward to the cap 13 in order to assist in expelling and dispensing ground material from the chamber 100.

Figure 2:
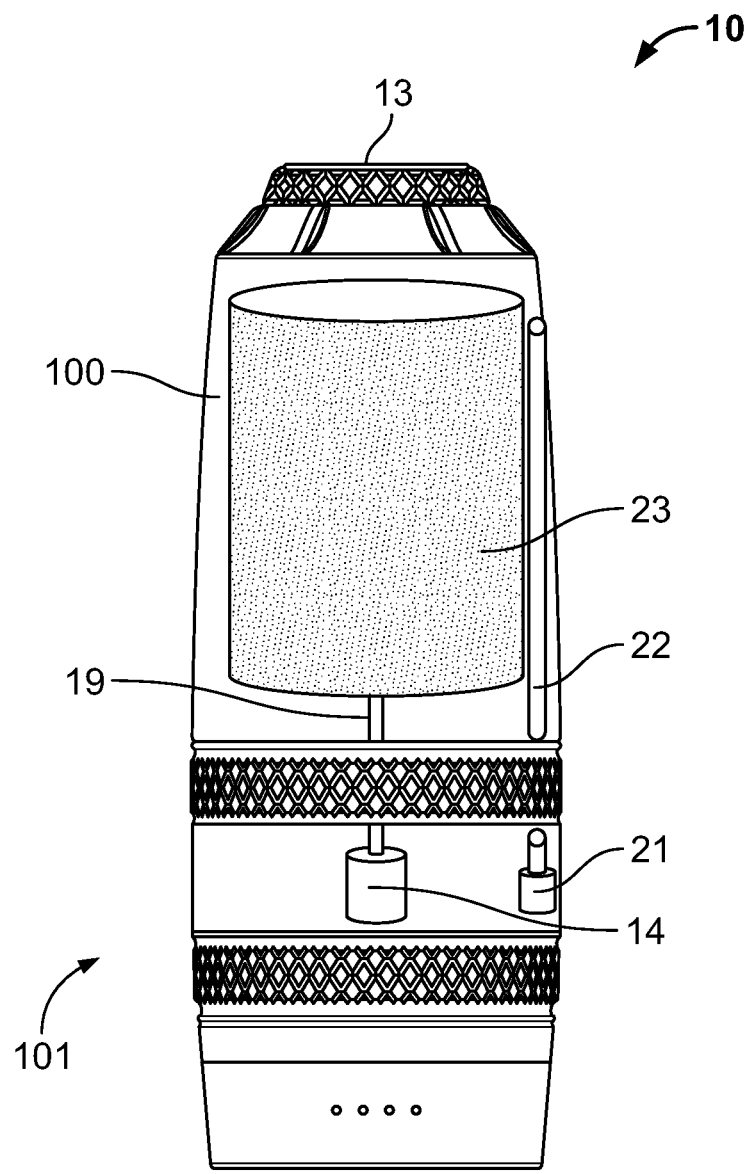
FIG. 2 is a schematic of the grinder showing a cleaning brush feature.

With reference to FIG. 2, shown is an embodiment of the grinder 10 configured with an air pump 21, air tube 22, and cleaning brush 23 which are configured to facilitate cleaning of the grinder 10. In some embodiments, the blade 17 and propeller 18 are removed from the drive shaft 19 and replaced with the cleaning brush 23. In some embodiments, the cleaning brush 23 comprises a drum or cylinder with bristles which agitate the interior of the chamber and chamber sidewalls for cleaning. In some embodiments, the motor 14 is configured to enter a low-speed "cleaning mode" such that the rotational speed is reduced from the typical grinding rotational speed, as further described below. To further facilitate cleaning, an electronic air pump 21 may be disposed inside the chamber 100. The air pump 21 is in air flow communication with the air tube 22, which air tube 22 extends upward from the air pump 21 along the inside of the chamber 100. In some embodiments, the air tube 22 contains one or more openings through with air is provided. The air pump can be used to generate air flow or suction within the chamber 100 to assist in the cleaning process and to dispense matter.

Figure 3:
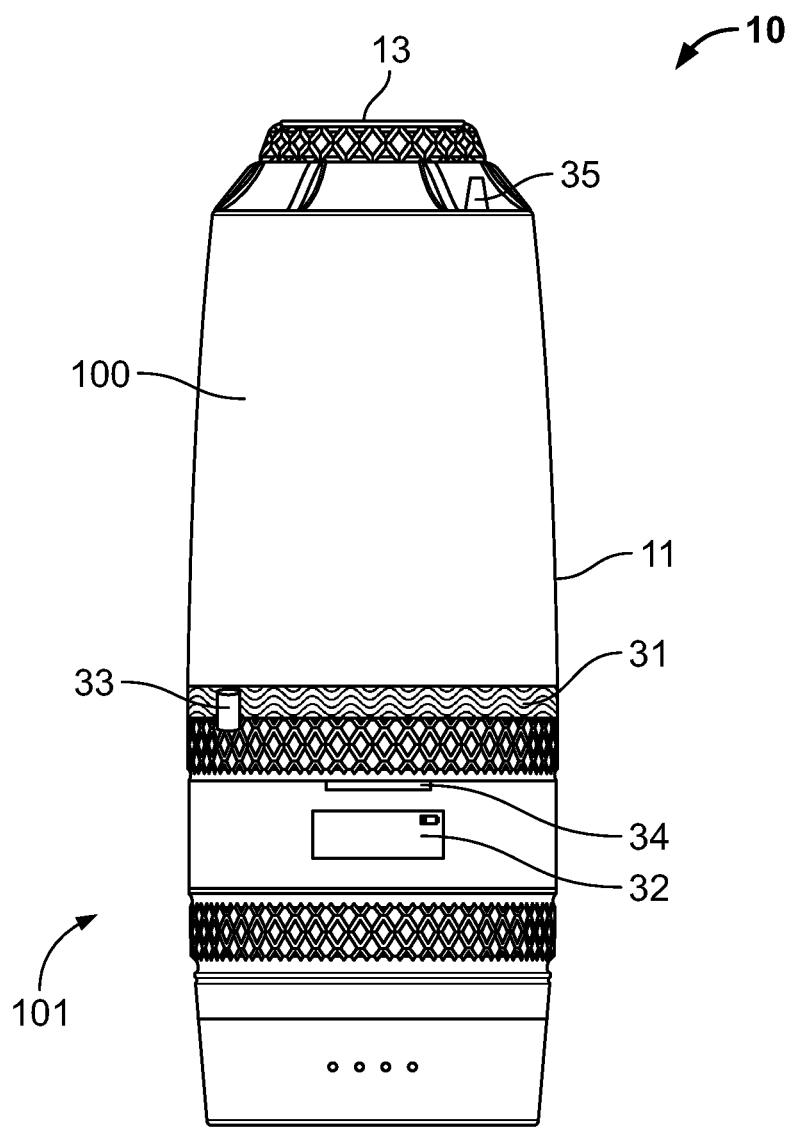
FIG. 3 is a schematic of the grinder showing a scale feature
Figure 4:
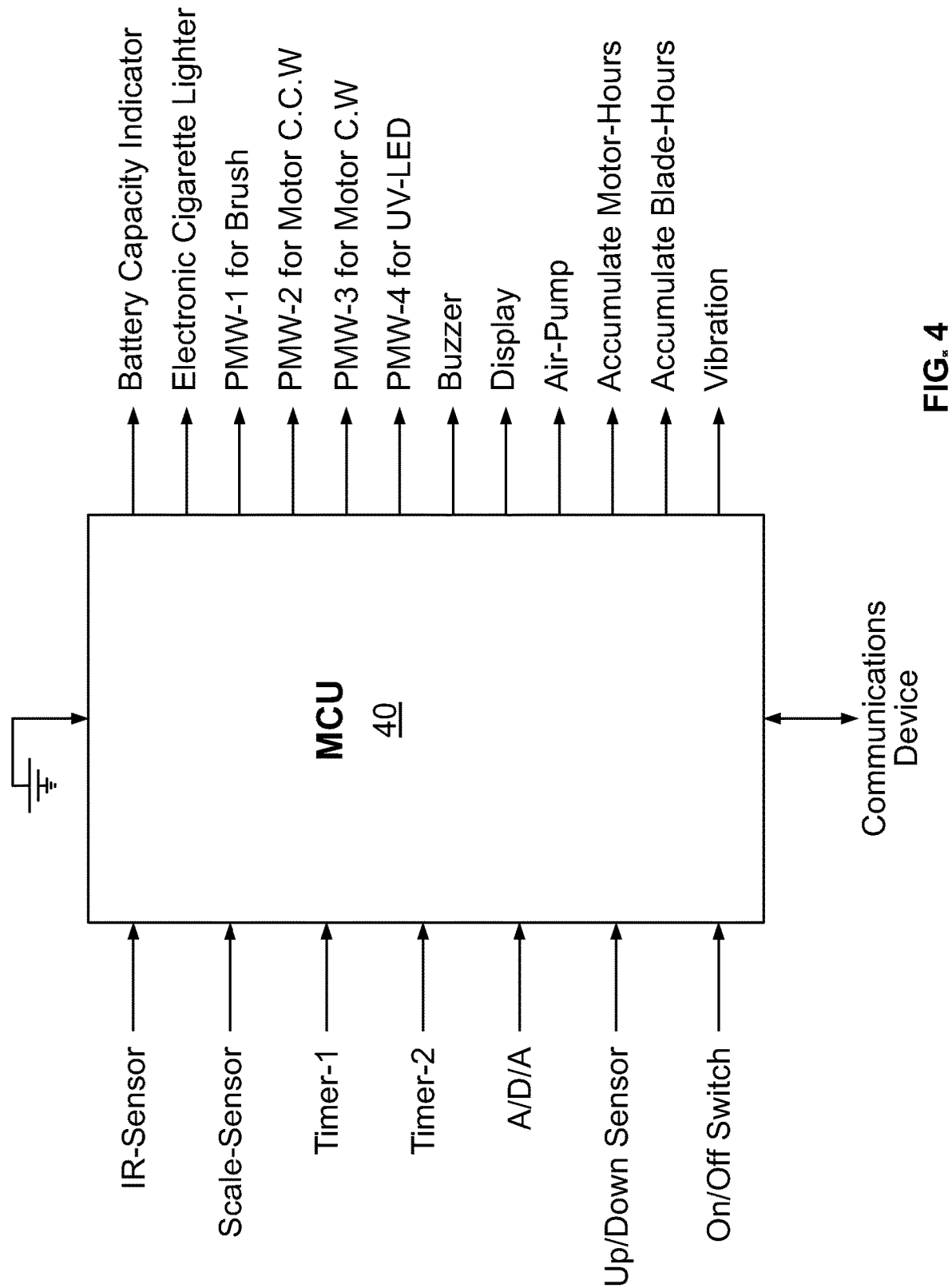
FIG. 4 is a schematic showing the electrical and other components of the grinder.

With reference to FIG. 3, shown are additional features and functionality. In some embodiments, the grinder 10 includes an electronic scale 31 disposed inside the chamber 100 in order to weigh the contents therein. The scale 31 comprises a scale transducer to measure the mechanical energy, i.e. the pressure applied to the scale 31 by the contents placed thereon, and converts the pressure to an electrical output (e.g. current or voltage differential). The electrical output at from the scale is processed into a digital signal by the microcontroller 40 (described below) which digital signal can then be outputted on display 32 or through a communications device. In some embodiments, in an infrared sensor 33 is provided which is enabled to detect the internal volume of the contents of chamber 100. In some cases, the infrared sensor 33 is configured to operate by a ball switch when the unit is turned upside down. In some embodiments, a vibration motor 34 is provided to agitate the contents of the chamber 100 to further facilitate grinding and dispensing functionality. As further described herein, the display 32 is configured to display a variety of information such as battery status, weight, volume, and other functions described herein.

In some embodiments, seated on the main housing 11 is a heating device 35 configured as a coil-type heating element. In some embodiments the heating device 35 is in electrical communication with the power supply 110 and receives current therefrom which heats the wire to a sufficient temperature to ignite a smoking implement such as a cigarette. In some embodiments, the heating device 35 is configured as a lighter and operated by a button 111 on the main housing 11 and thus the heating device 35 is in communication with the microcontroller 40 for such control functionality.

As noted, a microcontroller 40 inside the housing controls the action of the motor and provides an input/output interface by way of control buttons 111 on the grinder 10. In some embodiments, the microcontroller 40 also provides power and communication connectivity for other components such as the motor 14, the LED lights 15, the air pump 21, the scale 31, and the heating device 35. In some embodiments the microcontroller 40 is an embedded system and comprises a processor (CPU), memory, and control programming for the various input and output peripherals. The microcontroller is operable configured to provide overload protection, safety protection based on temperature or speed, and can manage smart charging functionality which allows the grinder to be operated while charging.

The microcontroller may also include a communications device such as a Wifi chip, a Bluetooth chip, a NFC chip, a Universal Serial Bus (USB) port, or combinations thereof. In some embodiments the communication device is configured to communicate with an external computing device such as a computer or smartphone in order to send and receive data including status information and commands. Such data transmission can be accomplished through a customized application running on the smartphone or computer. Charging of the power source 101 can also be accomplished through a wire connection such as USB or wireless charging (Qi and others).

The display 32 may be configured to display certain information including without limitation the battery level status, the weight of material in the chamber 100, the temperature of the heating device 35, or the like. Accordingly, the display may comprise LED, LCD, OLED, or the like and may output information as a digital alphanumerical readout or other indicators such as a series of lights. One or more buttons on the grinder 10 may function as power and/or control buttons for various features. In some embodiments, for safety purposes the user must press both two or more buttons simultaneously in order to activate the blade 17 (and/or propeller 18) and carry out a grinding operation.

Additional features of the microcontroller 40 include (1) an orientation sensor to detect whether the grinder is upright or upside down and thus to permit use of the infrared sensor 33 or other features; (2) one or more timers to time grinding operations or accumulated usage, which can be used to indicate wear on the blade and/or motor to detect and indicate that the blade and/or motor needs to be replaced; (3) an analog to digital converter and a digital to analog converter in order for various sensors and inputs/outs to communicate to and from the microcontroller 40 and its components; (4) a batter capacity detection circuit which corresponds to the indicator 16 on the housing 1; (5) one or more MOSFET which are used to control the voltage, frequency, amplitude and interval of the pulse width modulation (PWM) sent to the motor 14 and LED lights 15; and (6) an audible buzzer or alert responsive to various inputs and outputs of the system.

In some embodiments, the grinder includes connectivity features such that the communications device can communicate with an outboard smartphone or computer for added functionality. In some embodiments the grinder is "app-enabled" and works in conjunction with control and notification software. The user can utilize an application running on a smartphone or computer to obtain information from the grinder such as weight, battery status, or the like. In some embodiments, each time the grinder is turned the scale obtains a weight measurement and stores corresponding weight data in the memory of the microcontroller. Then, each time of the user loads the application on his computing device, the stored weight information is automatically synchronized to the application. The grinder can also be configured to send outbound alerts to advise the user that, for example, the weight of product in the grinder has dropped below a predetermined level. It can also store and display the original weight and the new weight after a dispensing operation. The application may also include functionality to permit the user to directly purchase new products to be used in conjunction with the grinder.

The materials selected for the grinder of the present invention are not particularly limiting however if the heating device 35 is included it may be desirable for at least a portion of main housing 11 to be comprised of a relatively heat resistant material or have some heat resistant material or compound embedded therein. Further in some embodiments at least a portion of the chamber 100 is comprised of a transparent material so that the user can easily observe the contents therein.

It is to be noticed that the term "comprising," used in the claims, should not be interpreted as being limitative to the means listed thereafter. Thus, the scope of the expression "a device comprising means A and B" should not be limited to devices consisting only of components A and B. It means that with respect to the present invention, the only relevant components of the device are A and B. Put differently, the terms "including", "comprising" and variations thereof mean "including but not limited to", unless expressly specified otherwise.

Similarly, it is to be noticed that the term "coupled", also used in the claims, should not be interpreted as being limitative to direct connections only. Thus, the scope of the expression "a device A coupled to a device B" should not be limited to devices or systems wherein an output of device A is directly connected to an input of device B. It means that there exists a path between an output of A and an input of B which may be a path including other devices or means.

The enumerated listing of items does not imply that any or all of the items are mutually exclusive, unless expressly specified otherwise. The terms "a", "an" and "the" mean "one or more", unless expressly specified otherwise.

Elements of the invention that are in communication with each other need not be in continuous communication with each other, unless expressly specified otherwise. In addition, elements of the invention that are in communication with each other may communicate directly or indirectly through one or more other elements or other intermediaries.

One skilled in the art will appreciate that the present invention can be practiced by other than the above-described embodiments, which are presented in this description for purposes of illustration and not of limitation. The specification and drawings are not intended to limit the exclusionary scope of this patent document. It is noted that various equivalents for the particular embodiments discussed in this description may practice the invention as well. That is, while the present invention has been described in conjunction with specific embodiments, it is evident that any alternatives, modifications, permutations and variations will become apparent to those of ordinary skill in the art in light of the foregoing description. Accordingly, it is intended that the present invention embrace all such alternatives, modifications and variations as fall within the scope of the appended claims. The fact that a product, process or method exhibits differences from one or more of the above-described exemplary embodiments does not mean that the product or process is outside the scope (literal scope and/or other legally-recognized scope) of the following claims.

What is claimed is:

1. An electronic grinder, comprising:
a main housing delimiting a chamber, wherein a distal end of the main housing is sealed by a cap;
the main housing including a motor;
a blade and a propeller removably connected to the motor, wherein the blade and the propeller extend into the chamber;
wherein, with the cap closed, the blade and propeller rotate in a first direction to grind material disposed in the chamber;
and wherein, with the cap open, the blade and propeller rotate in a second direction to generate air flow away from the blade and propeller and toward the distal end which facilitates dispensing of the material from the chamber.

2. The electronic grinder of claim 1, wherein the blade and propeller generate air flow toward the blade and propeller when rotating in the first direction.

3. The electronic grinder of claim 1, wherein the blade includes one or more curved blade elements.

4. The electronic grinder of claim 1, wherein the blade and propeller are removably connected to the motor by a magnetic connection.

5. The electronic grinder of claim 1, wherein the blade and propeller are replaced by a cleaning brush, the cleaning brush connected to the motor and configured to agitate and clean the inside of the chamber.

6. The electronic grinder of claim 1, including one or more LEDs disposed in the chamber, the LEDs configured to emit light in the range of 100-280 nm effective to kill microorganisms inside the chamber.

7. The electronic grinder of claim 1, including an air pump disposed in the chamber to generate air flow toward the distal end thereof.

8. The electronic grinder of claim 7, including an air tube in flow communication with the air pump to disperse air flow inside the chamber.

9. The electronic grinder of claim 1, including a heating device on the housing configured as a lighter.

10. The electronic grinder of claim 1, wherein the main housing includes a microcontroller and a power supply, the microcontroller configured to operate and control the motor.

11. The electronic grinder of claim 10, wherein the microcontroller includes a communications device operable to communicate with an external computing device.

12. The electronic grinder of claim 10, wherein the microcontroller is operably configured to provide over-load protection, safety protection based on temperature or speed, and can manage smart charging functionality which allows the grinder to be operated while charging.

13. The electronic grinder of claim 10, wherein the main housing includes a display and one or more control buttons, the display and the buttons each in communication with the microcontroller.

14. The electronic grinder of claim 13, wherein the display is configured to display a status of the power supply.

15. The electronic grinder of claim 10, wherein the chamber includes an electronic scale in communication with the microcontroller and configured to weigh contents inside the chamber.

16. The electronic grinder of claim 10, wherein the chamber includes an infrared volume sensor in communication with the microcontroller and configured to detect the volume of contents inside the chamber.

17. The electronic grinder of claim 10, including one or more timers in communication with the microcontroller to monitor usage of the motor, blade, and propellor.

18. The electronic grinder of claim 10, including an audible buzzer in communication with the microcontroller configured to trigger based on predetermined inputs and outputs of the microcontroller.

19. The electronic grinder of claim 10, including a vibration motor in communication with the microcontroller configured to trigger based on predetermined inputs and outputs of the microcontroller.

20. The electronic grinder of claim 10, wherein the microcontroller is configured to adjust the speed of the motor for at least a grinding setting, a dispensing setting, and a cleaning setting, wherein the in the cleaning setting the rotational speed of the motor is less than both the grinding setting and the dispensing setting.

* * * * *